(12) United States Patent
Starnes

(10) Patent No.: US 7,670,352 B1
(45) Date of Patent: Mar. 2, 2010

(54) ADJUSTABLE TIP WITH INTEGRATED DETENT FOR BLOOD LANCET SYSTEM

(75) Inventor: Charles D. Starnes, Coral Springs, FL (US)

(73) Assignee: Caribbean Medical Brokers, Inc., Coral Springs, FL (US)

( * ) Notice: Subject to any disclaimer, the term of this patent is extended or adjusted under 35 U.S.C. 154(b) by 1061 days.

(21) Appl. No.: 10/896,655

(22) Filed: Jul. 22, 2004

Related U.S. Application Data

(60) Provisional application No. 60/555,865, filed on Mar. 24, 2004.

(51) Int. Cl.
*A61B 17/32* (2006.01)
(52) U.S. Cl. ........................... 606/181; 600/583
(58) Field of Classification Search ................ 623/1.15; 606/181–186; 600/583, 1.15; 222/519–521, 222/549
See application file for complete search history.

(56) References Cited

U.S. PATENT DOCUMENTS

| | | | |
|---|---|---|---|
| 3,086,530 A | 4/1963 | Groom | |
| 3,358,689 A | 12/1967 | Higgins | |
| 3,612,051 A | 10/1971 | Arce | |
| 4,469,110 A | 9/1984 | Slama | |
| 4,895,147 A | 1/1990 | Bodicky et al. | |
| 4,967,941 A * | 11/1990 | Beck | 222/521 |
| 5,100,427 A | 3/1992 | Crossman et al. | |
| 5,207,699 A | 5/1993 | Coe | |
| 5,318,584 A | 6/1994 | Lange et al. | |
| 5,324,303 A | 6/1994 | Strong et al. | |
| 5,385,571 A | 1/1995 | Morita | |
| 5,423,847 A | 6/1995 | Strong et al. | |
| 5,464,418 A | 11/1995 | Schraga | |
| 5,554,166 A | 9/1996 | Lange et al. | |
| 5,613,978 A | 3/1997 | Harding | |
| 5,628,765 A | 5/1997 | Morita | |
| 5,730,753 A | 3/1998 | Morita | |
| RE35,803 E | 5/1998 | Lange et al. | |
| 5,873,887 A | 2/1999 | King et al. | |
| 5,916,230 A | 6/1999 | Brenneman et al. | |
| 5,984,940 A | 11/1999 | Davis et al. | |
| 6,022,366 A | 2/2000 | Schraga | |
| 6,045,567 A | 4/2000 | Taylor et al. | |
| 6,056,765 A | 5/2000 | Bajaj et al. | |
| D428,150 S | 7/2000 | Ruf et al. | |
| 6,156,051 A | 12/2000 | Schraga | |
| 6,258,112 B1 | 7/2001 | Schraga | |
| 6,322,575 B1 | 11/2001 | Schraga | |
| 6,346,114 B1 | 2/2002 | Schraga | |
| 6,419,661 B1 | 7/2002 | Kuhr et al. | |

(Continued)

FOREIGN PATENT DOCUMENTS

CN 01263172.8 6/2002

*Primary Examiner*—(Jackie) Tan-Uyen T. Ho
*Assistant Examiner*—Gregory Anderson
(74) *Attorney, Agent, or Firm*—Thomas C. Saitta

(57) ABSTRACT

Disclosed is an adjustable tip for a blood lancet device that is adjustable between several distances for varying the depth of skin puncture by a lancet needle. The adjustable tip includes a sleeve having a helical groove with spaced depressions and an end cap placed over and attached to the sleeve. The end cap includes a lug that fits with the helical groove of the sleeve to secure the end cap to the sleeve.

32 Claims, 8 Drawing Sheets

U.S. PATENT DOCUMENTS

| | | |
|---|---|---|
| 6,432,120 B1 | 8/2002 | Teo |
| 6,451,040 B1 | 9/2002 | Purcell |
| 6,514,270 B1 | 2/2003 | Schraga |
| 6,530,937 B1 | 3/2003 | Schraga |
| 6,537,292 B1 | 3/2003 | Lee |
| 6,558,402 B1 | 5/2003 | Chelak et al. |
| 6,589,261 B1 | 7/2003 | Abulhaj et al. |
| 6,602,268 B2 | 8/2003 | Kuhr et al. |
| 6,706,049 B2 | 3/2004 | Moerman |
| 6,723,111 B2 | 4/2004 | Abulhaj et al. |
| 2004/0039408 A1 | 2/2004 | Abulhaj et al. |
| 2004/0059365 A1 | 3/2004 | Abulhaj et al. |

* cited by examiner

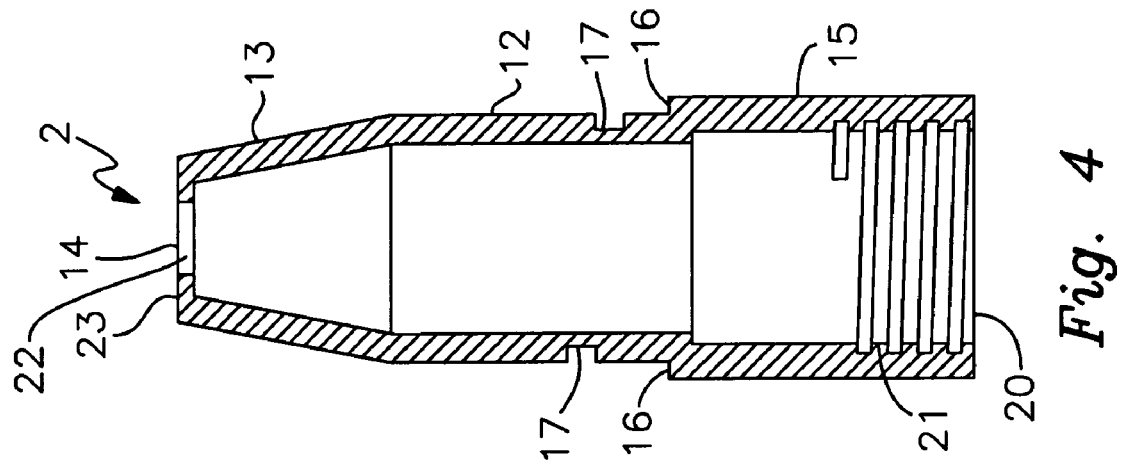
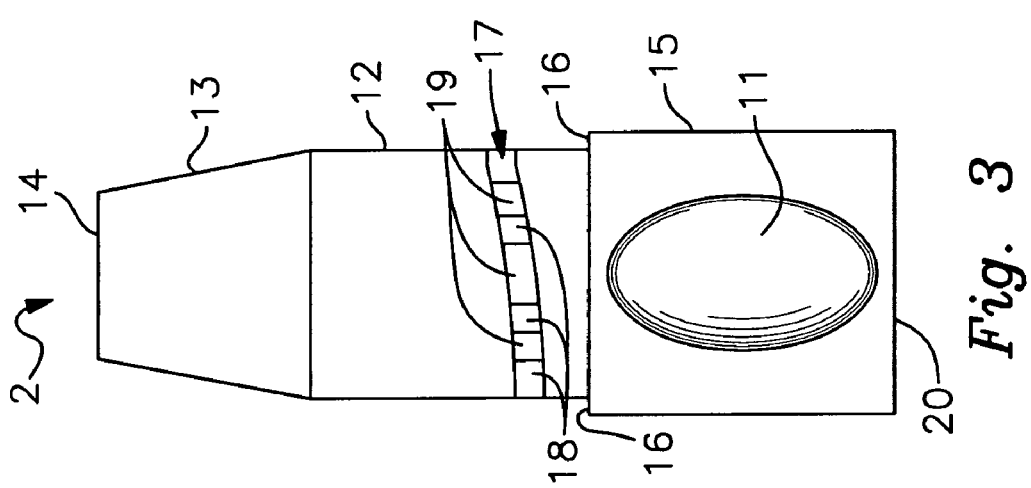
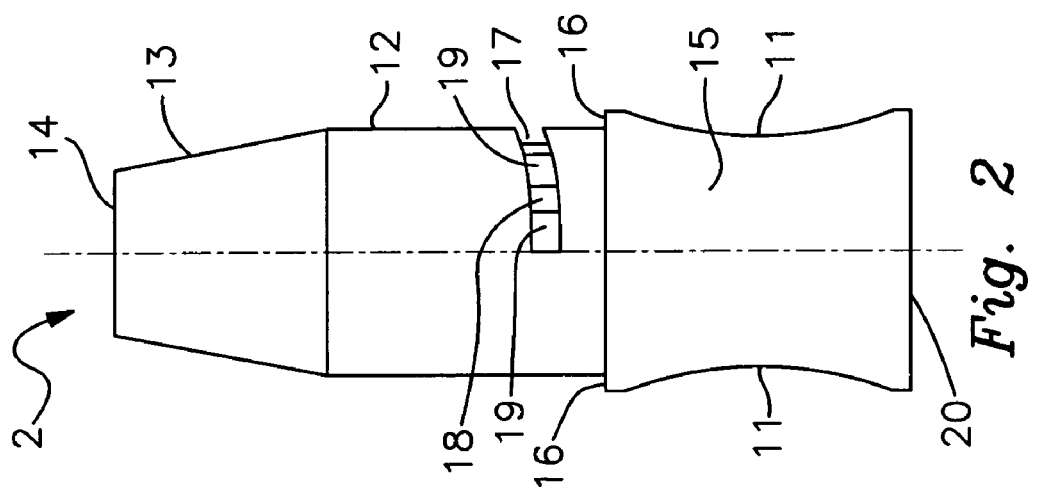

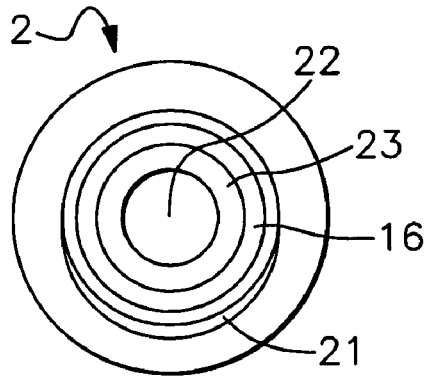
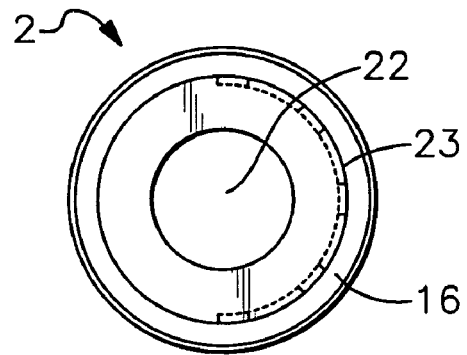
Fig. 5
Fig. 6
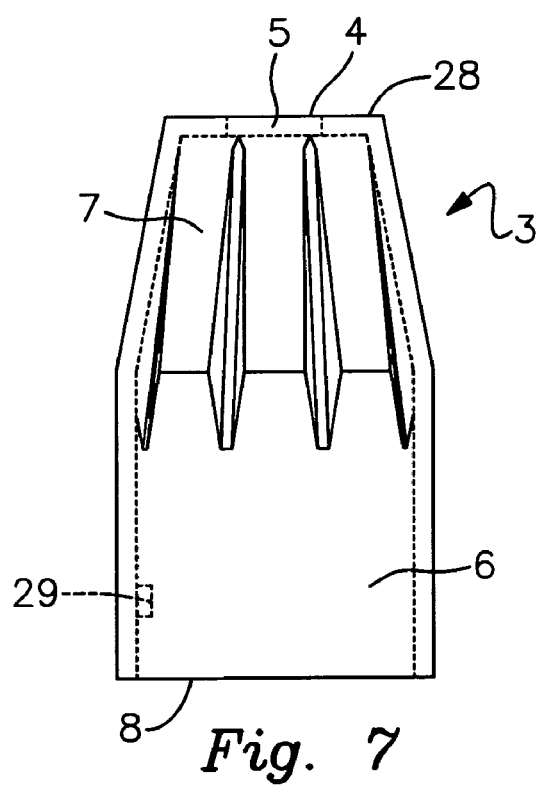
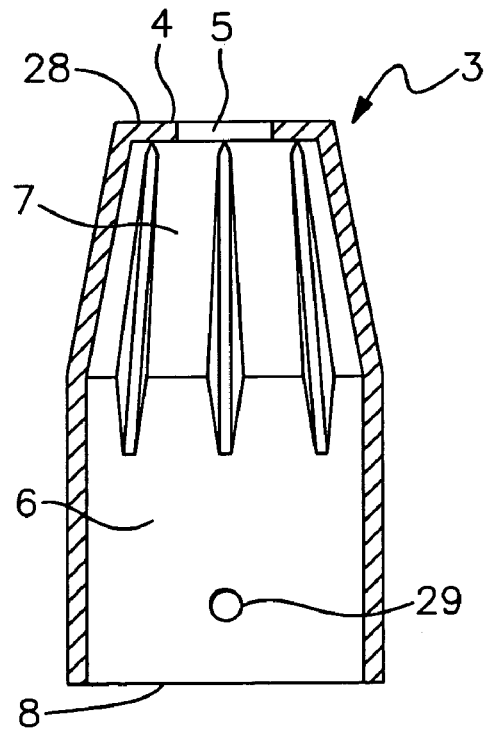
Fig. 7
Fig. 8

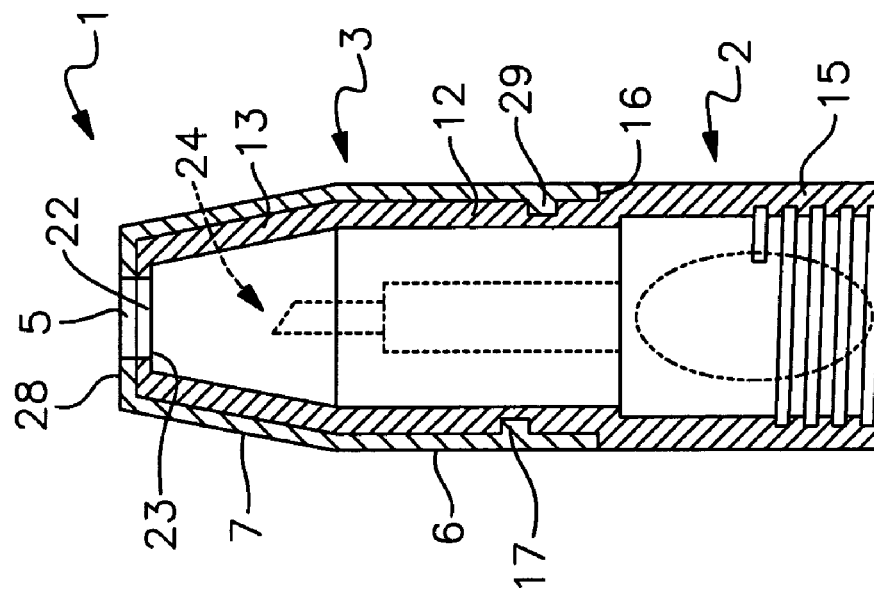
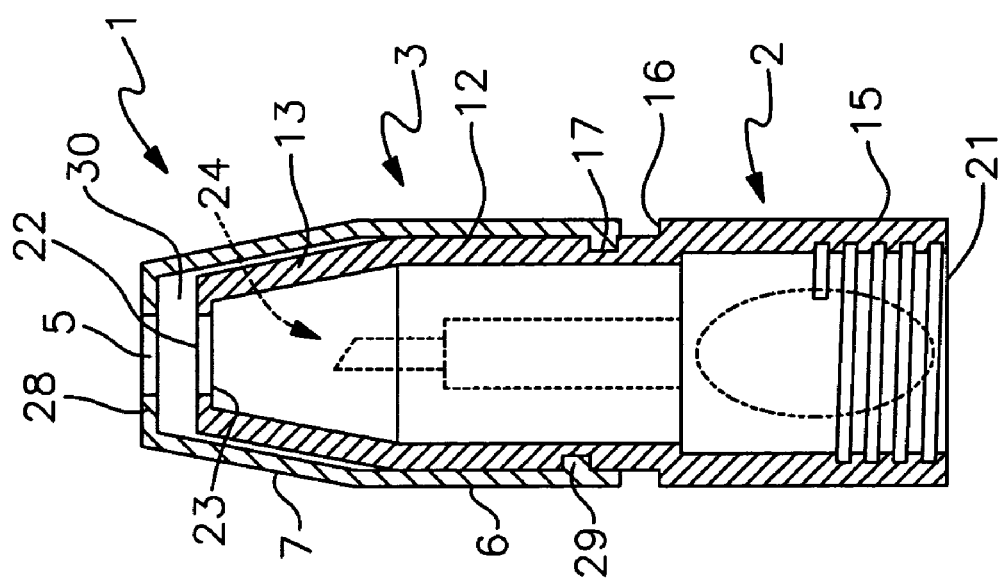

ADJUSTABLE TIP WITH INTEGRATED DETENT FOR BLOOD LANCET SYSTEM

REFERENCE TO RELATED APPLICATION

Priority to the filing date of U.S. provisional patent application Ser. No. 60/555,865 filed on Mar. 24, 2004 is hereby claimed and which is incorporated by reference herein in its entirety.

BACKGROUND OF THE INVENTION

1. Technical Field

The present invention relates in general to the field of medical lancet devices used for obtaining droplets of blood samples for testing and diagnostic applications. More particularly, the invention relates to a tip for a blood lancet device that is adjustable between several distances for varying the depth of skin puncture by a lancet needle.

2. Description of the Related Art

The use of lancets and lancing devices are well known in the art as a convenient and safe means for piercing or pricking a person's skin to draw small amounts blood that can then be subjected to a variety of medical tests such as for blood sugar content. A typical integrated lancet design is described in U.S. Pat. No. 3,358,689, with a lancet needle encased in an elongated plastic body. Known integrated lancet assemblies having adjustable tips are described in U.S. Pat. Nos. 6,530,937 and 6,558,402 and 5,916,230 and 6,419,661. Typical lancet assemblies depict a cylindrical housing containing a spring-loaded assembly that is activated by a button on the housing's exterior surface. Upon activation, the lancet needle is thrust deeper into the unit's tip and the needle protrudes from an opening on the top of the tip. The lancet needle exits the opening for puncturing a patient's skin. Following activation and extension of the lancet needle through the tip opening, the spring retracts to its natural state of equilibrium and causes the lancet to retract inwards. When the spring is at rest, the needle tip no longer extends through the tip opening. The tip is necessarily removable so that a used lancet may be removed and discarded and a fresh lancet inserted into the tip for the next use. In one common design, the unit is pen-shaped and has a screw-on tip for easy removal. Lancet devices having this configuration are disclosed in U.S. Pat. Nos. 6,558,402 and 5,613,978

Lancing devices are designed to draw a relatively minute quantity of blood from capillaries immediately below the surface of the skin and are commonly used by patients is themselves at home as well as by medical professionals in medical offices and hospitals.

These devices are also used in medical office and hospital settings in order avoid the necessity of having to re-sterilize the mechanical device and/or lancet after each use. Lancing devices are specifically designed to safely accommodate their purpose as "pricking" devices that are commonly utilized by non-medically trained individuals including children. Specifically, in order to effectuate a safe and controlled puncturing of a patient's skin, the exposed tip of the needle extends only a very short distance (typically a few millimeters) from the flat upper surface of the lancet body, which acts as a bearing to limit the puncture depth.

A problem arises, however, concerning the depth of the lancet needle extending from the lancet assembly and the depth of the corresponding penetration it makes into a patients' skin. Lancet devices that do not allow for adjusting the depth of penetration can be undesirable. There is a need for an adjustable depth lancet device to accommodate patients having different skin thicknesses and different levels of pain tolerance.

For example, Chinese Patent ZL 01263172.8 discloses an adjustable head lancet tip. However, the invention of that reference utilizes five separate components: an end cover and an adjustable shell comprised of a front cover, a rear ring, and a split barrel having upper and lower sides. This unit is complex and requires several steps during manufacturing and assembly. After molding, the adjustable shell's four components must be assembled and permanently joined using the added step of applying a sealing method such as sonic welding. The newly formed and assembled adjustable shell must also be mounted onto the end cover. Additionally, the disclosure teaches the use of two separate and independent components for effectuating the varying length of the tip and for creating the detent that holds the tip at each depth setting. Thus, this reference does to not teach an assembly that provides a single functional unit for accomplishing both of these features in a manner that can be manufactured using only two molded pieces that may be snapped together without the added step of sonic welding.

U.S. Pat. No. 6,451,040 discloses an adjustable lancet device end cap. The disclosure of this reference teaches the use of a base cap and an end cap to accomplish adjustability and the detent. However, like the Chinese reference described above, those features are accomplished separately and independently. The reference discloses the use of one or more fingers located on the end cap, and the detent is positioned on a post located on the end cap that comes into clicking contact with slots formed on the twist cap. Additionally, the apparatus, as depicted in this reference is relatively complex and not suitable for attachment to generally available cylindrically shaped lancet devices.

It can therefore be appreciated that a need exists for an improved lancing design that overcomes the foregoing problems. The present invention addresses such needs.

A primary object of the invention is to provide an adjustable tip for a blood lancet device capable of use with conventional and generally available and relatively inexpensive lancets.

A further object of the invention is to provide an adjustable tip for a blood lancet device capable of use with conventional and generally available and relatively inexpensive lancet devices, whereby an existing lancet devices' tip may be readily replaced by the adjustable tip of the present invention.

A further object of the invention is to provide an adjustable tip for a blood lancet device which is simple in design and relatively inexpensive to manufacture by only using two parts that may be snapped together.

A further object of the invention is to provide an adjustable tip for a blood lancet device which provides a visible indication of each of the various depths of skin puncture so the user can accurately set the adjustable tip prior to usage.

A further object of the invention is to provide an adjustable tip for a blood lancet device which provides an audible indication when the tip is adjusted from one depth to another so the user can readily and easily confirm when the tip has been adjusted to a different depth.

A further object of the invention is to provide an adjustable tip for a blood lancet device which provides a tactile sensory indication when the tip is adjusted from one depth to another so the user can readily and easily confirm when the tip has been adjusted to a different depth.

A further object of the invention is to provide an adjustable tip for a blood lancet device wherein the means for adjusting the tip, the means for holding the tip in each particular position and the means for indicating to the user that the tip has been adjusted to another depth setting are all integrated as a single functional unit within the tip.

A further object of the invention is to provide an adjustable tip for a blood lancet device which provides stabilization of the adjustable tip such that the tip remains locked at each particular depth setting and avoids slipping and resulting punctures at unintended depths.

SUMMARY

Briefly, the present invention includes an adjustable tip for a blood lancet device that is adjustable between several distances for varying the depth of skin puncture by a lancet needle. The adjustable tip includes a sleeve having a helical groove with spaced depressions and an end cap placed over and attached to the sleeve. The end cap includes a lug that fits within the helical groove of the sleeve to secure the end cap to the sleeve.

In greater detail, the spaced depressions include peaks and valleys in which the lug resides within the valleys as the end cap is twisted up or down the outside of the sleeve. The spaced depressions may be evenly spaced to form substantially equidistant and repeating peaks and valleys. Typically, the helical groove includes a spiral of at least 180 degrees around a circumference of the sleeve. Additionally, visual indicators may be located on the exterior surface of the end cap and/or the exterior surface of the sleeve.

A further embodiment of the present invention includes an adjustable tip for a lancet comprising a sleeve whose exterior walls include a lug that operatively fits within a helical groove of an end cap. The end cap fits over the sleeve and is guided along the sleeve by the helical groove and lug combination. The helical groove includes spaced depressions that have both peaks and valleys. The depressions can be evenly spaced to form substantially equidistant and repeating peaks and valleys. The lug typically resides within the valleys.

An additional embodiment of the present invention includes a lancet assembly. The lancet assembly includes an adjustable tip attached to a lancet. The adjustable tip includes a sleeve having a helical groove and an end cap fitted over the sleeve. The end cap also includes a lug which fits within the helical groove of sleeve, thus securing the end cap to the sleeve. The lancet includes a body having a shoulder and a needle extending from the shoulder. Additionally, the sleeve includes an opening formed in a top wall of the sleeve wherein the body portion of the lancet is prevented from extending outward from the opening by the top wall.

The invention, as well as a preferred mode of use, further objects and advantages thereof, will best be understood by reference to the following detailed description of an illustrative embodiment when read in conjunction with the accompanying drawings.

BRIEF DESCRIPTION OF THE DRAWINGS

In the drawings:

FIG. 2 depicts a side view of sleeve 2;
FIG. 3 depicts another side view of sleeve 2;
FIG. 4 illustrates a cross-sectional view of sleeve 2 viewed from the opposite side depicted in FIG. 3;
FIG. 5 depicts a bottom view of sleeve 2;
FIG. 6 depicts a top view of sleeve 2;
FIG. 7 depicts a side view of end cap 3;
FIG. 8 depicts a cross-sectional view of end cap 3.
FIG. 13 depicts a cross-sectional view of an adjustable tip with integrated detent for blood lancet system in accordance with the present invention wherein end cap 3 is fully extended from sleeve 2 and the adjustable tip has been set to minimize the depth of lancet needle 27 upon activation;
FIG. 14 depicts a cross-sectional view of an adjustable tip with integrated detent for blood lancet system in accordance with the present invention wherein end cap 3 is fully retracted towards sleeve 2 and the adjustable tip has been set to maximize the depth of lancet needle 27 upon activation.

DETAILED DESCRIPTION

Figure 1A:
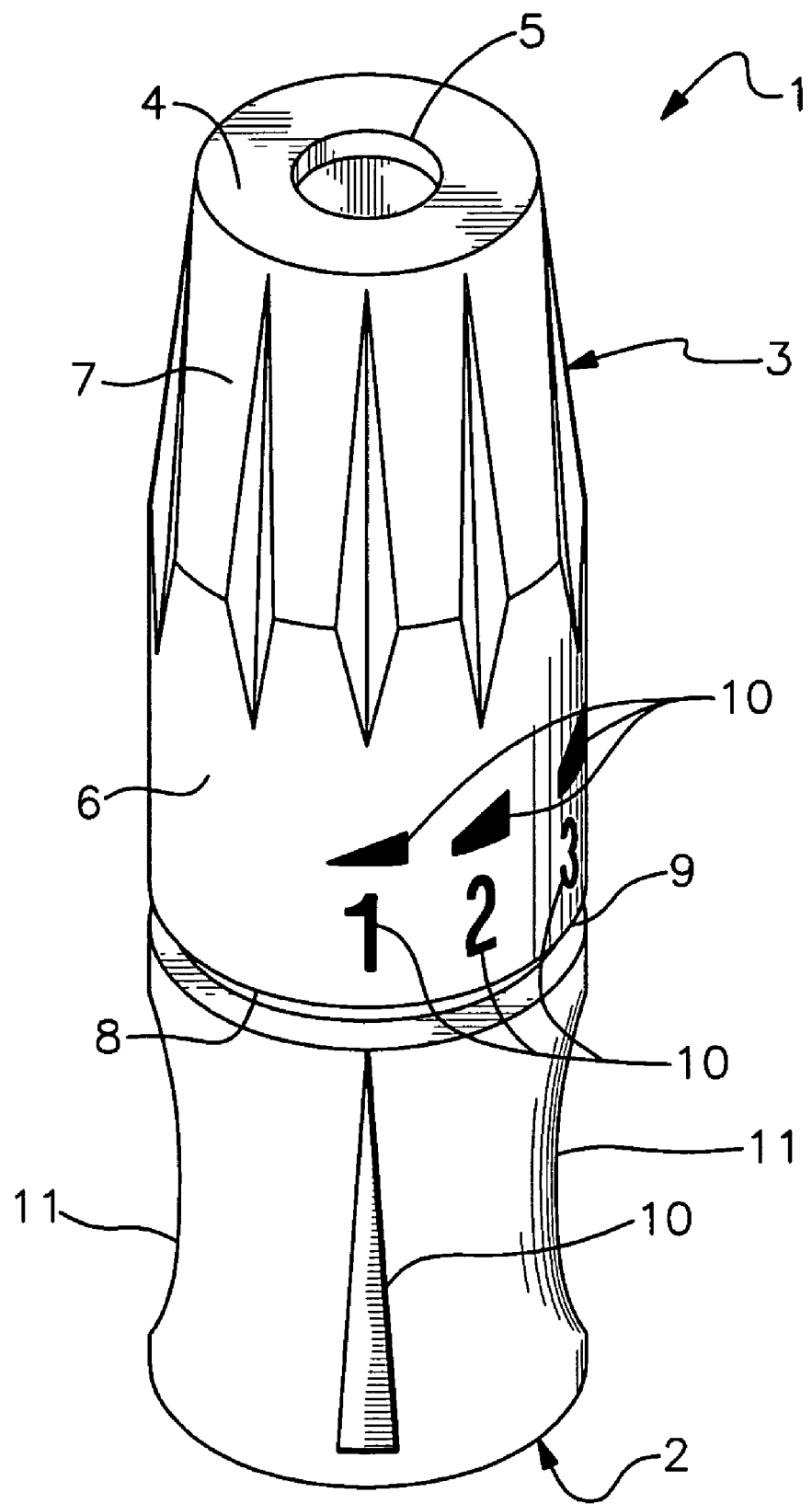
FIG. 1a illustrates an adjustable tip with integrated detent for blood lancet system in accordance with the present invention wherein end cap 3 is fully extended from sleeve 2 and the adjustable tip has been set to minimize the depth of lancet needle 27 upon activation.
Figure 1B:
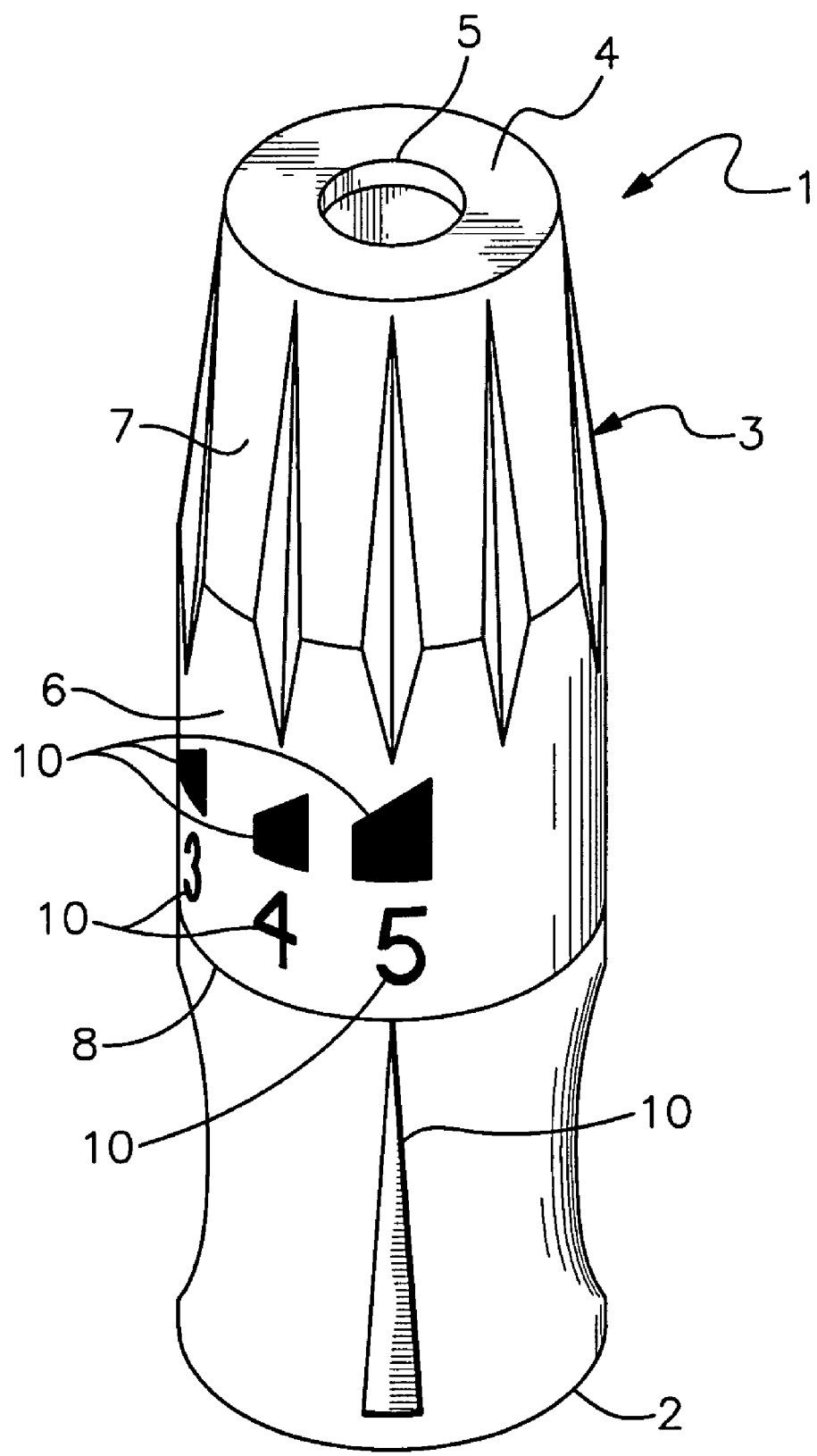
FIG. 1b illustrates an adjustable tip with integrated detent for blood lancet system in accordance with the present invention wherein end cap 3 is fully retracted towards sleeve 2 and the adjustable tip has been set to maximize the depth of lancet needle 27 upon activation.

The attached FIGS. 1-11 and 13-14 show an adjustable tip with integrated is detent for blood lancet system according to the present invention. FIGS. 1a and 1b show perspective views of an adjustable tip 1. Adjustable tip 1 is comprised of a sleeve 2 and an end cap 3. End cap 3 has a proximal end 4 which has an opening 5 at its center. The body portion of end cap 3 is comprised of a round section 6 and a tapered section 7. Tapered section 7 tapers towards proximal end 4 and round section 6 extends towards distal end 8. The interior of end cap 3 is a hollow cavity and is open on the bottom side at distal end 8 and at opening 5 at proximal end 4.

End cap 3 fits over sleeve 2. As will be discussed in further detail below, the top portion of sleeve 2 is shaped similarly to end cap 3 likewise having a round section and a tapered section such that those corresponding structures are received within the interior hollow cavity of end cap 3 and are correspondingly fitted against round section 6 and tapered section 7.

As will be discussed below, end cap 3 rotates about sleeve 2 such that each partial rotation results in end cap 3 partially spiraling in an upward direction away from sleeve 2 or partially spiraling in a downward direction depending on the direction of the rotation. FIG. 1a depicts end cap 3 in an upward position, thereby increasing the overall length of adjustable tip 1 and forming a gap 9 between end cap 3 and sleeve 2. As will be discussed below, this increased distance between end cap 3 and sleeve 2 provides depth control of a lancet needle and lancet device to which the invention attaches. FIG. 1b depicts end cap 3 in its maximum downward position, thereby minimizing the length of adjustable tip 1 and eliminating gap 9. As will be discussed below, this minimum distance between end cap 3 and sleeve 2 provides depth control and maximum penetration of a lancet needle and lancet device to which the invention attaches.

The surface of end cap 3 and sleeve 2 may also contain visual indicators 10 corresponding to the amount of rotation and extension between these two components and the puncture depth of a lancet needle. A portion of visual indicators 10 are located on both end cap 3 and sleeve 2 such that a differential is visibly observable upon rotating end cap 3 about sleeve 2. In the preferred embodiment, visual indicators 10 are comprised of numerals and corresponding graphics depicting the needle depth located on end cap 3 and an arrow/pointer located on sleeve 2. The arrow/pointer is in visible alignment with the needle depth indicator located on end cap 3 such that a user can readily determine each setting. However, any type of visual indicators may be used, such as lines, geometric patterns, images of needle length and pointers, arrows or notches. Likewise, visual indicators 10 appearing on end cap 3 and sleeve 2 may be reversed such that the depth indicator is located on sleeve 2 and a pointer on end cap 3.

To aid with adjusting adjustable tip 1 between settings, the bottom portion of sleeve 2 contains one or more depressions 11 to enable a user to grip sleeve 2 using two fingers, such as a thumb and index finger of the same hand. The preferred embodiment contains two depressions 11 on opposite sides of sleeve 2. Alternatively, the exterior surface of sleeve 2 may contain one or more grooves or a tacky surface for gripping with a user's fingers. Likewise, the exterior surface of end cap 3 may also contain one or more grooves or a tacky surface for gripping with a user's fingers. In one embodiment, grooves or elongated ridges are spaced and longitudinally located on the surface of tapered section 7 and extend into round section 6 of end cap 3.

FIGS. 2 and 3 show two different side views of sleeve 2. Sleeve 2 is comprised of a round section 12 and a tapered section 13. One end of tapered section 13 tapers towards proximal end 14 of sleeve 2 and its opposite end is joined with round section 12. The other end of round section 12 is mounted on base 15. Base 15 is rounded and has a girth larger than the girth of round section 12 thereby forming a circular shoulder 16 around the junction between base 15 and round section 12. Round section 12 contains a helical groove 17. In the preferred embodiment and as depicted in the Figures, helical groove 17 extends the length of half the circumference of round section 12. The 180 degree extension of helical groove 17 about round section 12 enables end cap 3 to rotate about sleeve 2 by 180 degrees or by a one-half turn. The interior wall of helical groove 17 is formed with evenly spaced depressions that form equidistant and repeating square shaped peaks 18 and valleys 19. Base 15 also contains one or more depressions 11 as previously described. Sleeve 2 may be manufactured using one or more of a variety of suitable materials such as semi-rigid plastics, which are suitable for manufacturing using well-known injection molding manufacturing techniques. Sleeve 2 may likewise be formed as a single molded plastic piece.

Figure 12:
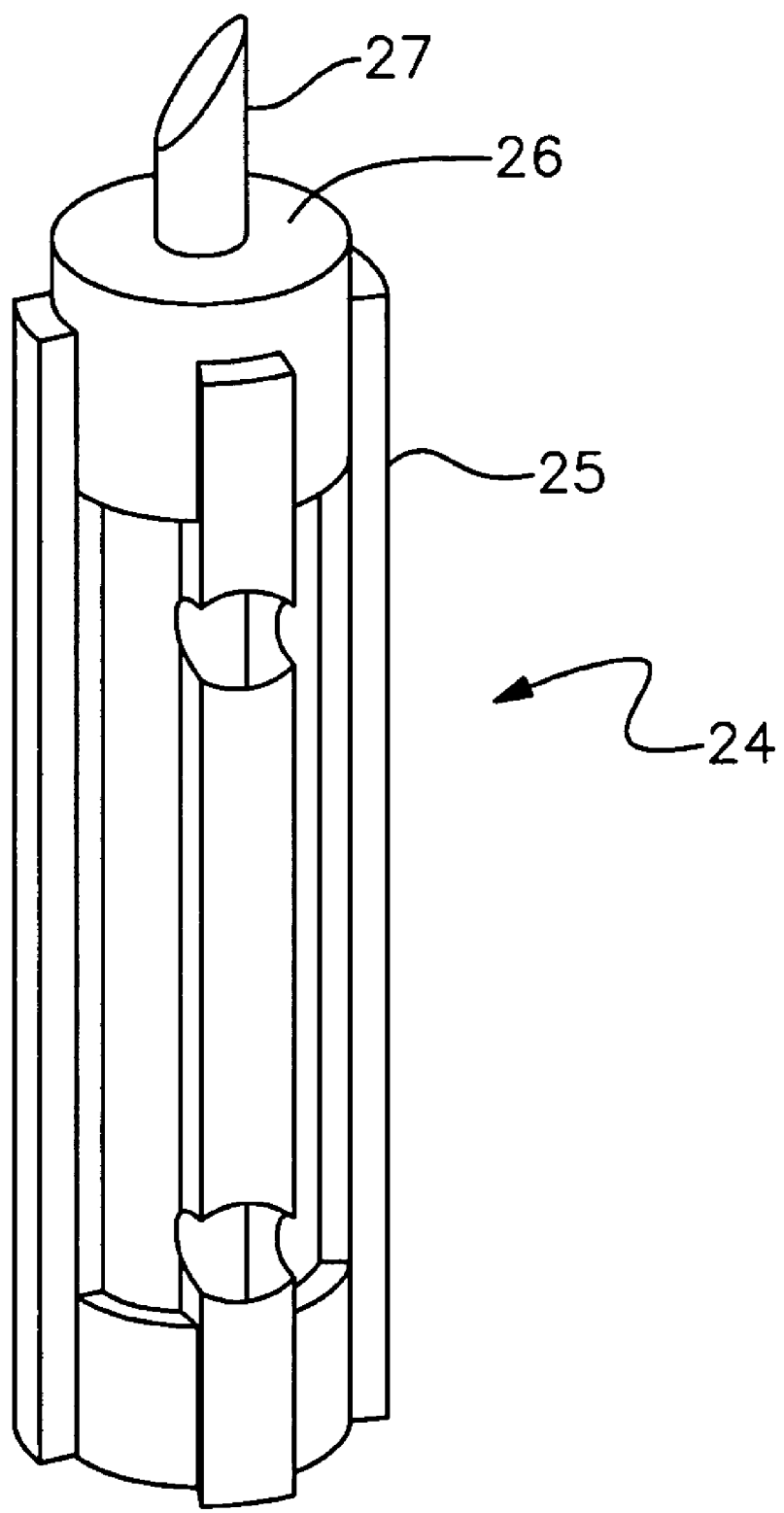
FIG. 12 illustrates a lancet that may be used with the present invention.

FIG. 4 shows a cross-section view of sleeve 2. Helical groove 17 extends 180 degrees around one-half the circumference of round section 12. The interior of Sleeve 2 is a hollow cavity that opens at proximal end 14 and at distal end 20. Sleeve 2 is partially closed by a top wall 23 at proximal end 14 and defines an opening 22. The periphery of top wall 22 is sized such that a lancet needle may pass through opening 22. A conventional lancet 24 is depicted in FIG. 12 and comprises a body portion 25 and a needle 27 extended from the center of one end. Lancet 24 further comprises a shoulder 26 on the end from which needle 27 extends. Opening 22 and top wall 23 are sufficiently spaced such that needle 27 is in communicable alignment and extends through opening 22 when the lancet device is activated and lancet 24 is thrust towards proximal end 14 of sleeve 2 during use. Body portion 25 is prevented from extending outward from opening 22 by top wall 23. During use, the interior surface of top wall 23 makes contact with shoulder 26 thereby providing a stop such that only needle 27 is capable of extending or otherwise protruding outward through opening 22.

Base 15 also contains an attachment means 21 located near the opening at distal end 20 for securing adjustable tip 1 to a lancet device. In the preferred embodiment and as depicted in FIG. 4, the attachment means is a screw thread for screwing adjustable tip 1 onto a pen-shaped lancet device such as the devices depicted in U.S. Pat. Nos. 6,558,402 and 5,613,978. Attachment means 21 may also comprise any other methods of securing two components together such as snaps, clips, glue, adhesives, sonic or thermal welding or bonding, flexible fasteners or screws.

FIG. 5 shows a bottom view of sleeve 2 and depicts the interior of the hollow cavity. Visible from this angle is opening 22, which is formed about the periphery of top wall 23, shoulder 16 and attachment means 21. FIG. 6 shows a top view of sleeve 2 and depicts opening 22 formed by the periphery of top wall 23, and shoulder 16.

FIGS. 7 and 8 show a side view and a cross-section side view of end cap 3, respectively. End cap 3 contains an interior hollow cavity that is open at both proximal end 4 and distal end 8. End cap 3 includes a top wall 28 having a periphery that forms opening 5. Opening 5 is in communicable alignment with opening 22 of sleeve 2 when end cap 3 is placed over sleeve 2 and the two form an integral assembly. The circumference of opening 5 is sufficiently sized such that needle 27 can extend through without making contact with the edges or sidewalls of top wall 28 during use. End cap 3 further comprises a lug 29 affixed to the interior wall of round section 6. Lug 29 is sufficiently sized to fit completely within helical groove 17 of sleeve 2. Lug 29 is positioned on the interior wall of round section 6 to correspond with the position of helical groove 17 on round section 12 of sleeve 2. When end cap 3 and sleeve 2 are combined into an integral assembly, lug 29 snugly fits and snaps into helical groove 17 and locks together the two components. Lug 29 extends outward from the interior wall of round section 6 a sufficient distance such that the outermost edge of lug 29 makes contact with peaks 18 and valleys 19 during rotation of end cap 3. End cap 3 may be manufactured using one or more of a variety of suitable materials such as semi-rigid plastics, which are suitable for manufacturing using well-known injection molding manufacturing techniques. End cap 3 may likewise be formed as a single molded plastic piece.

Figure 9:
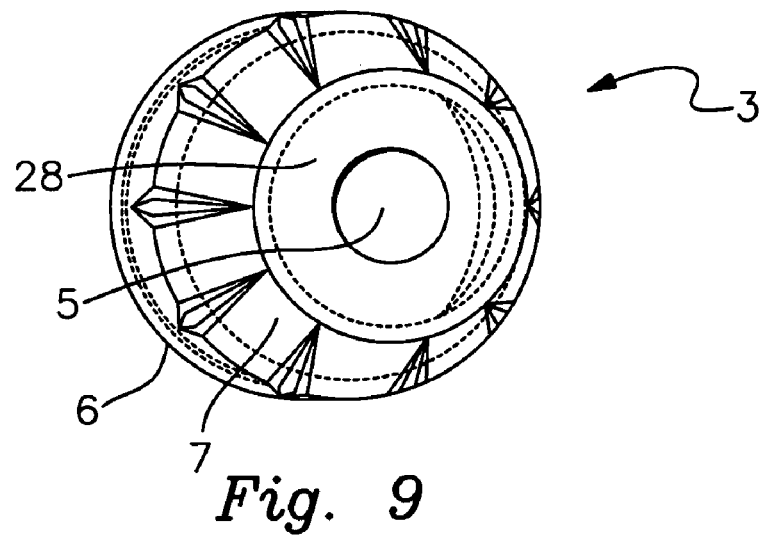
FIG. 9 illustrates a top perspective view of end cap 3.
Figures 10, 11:
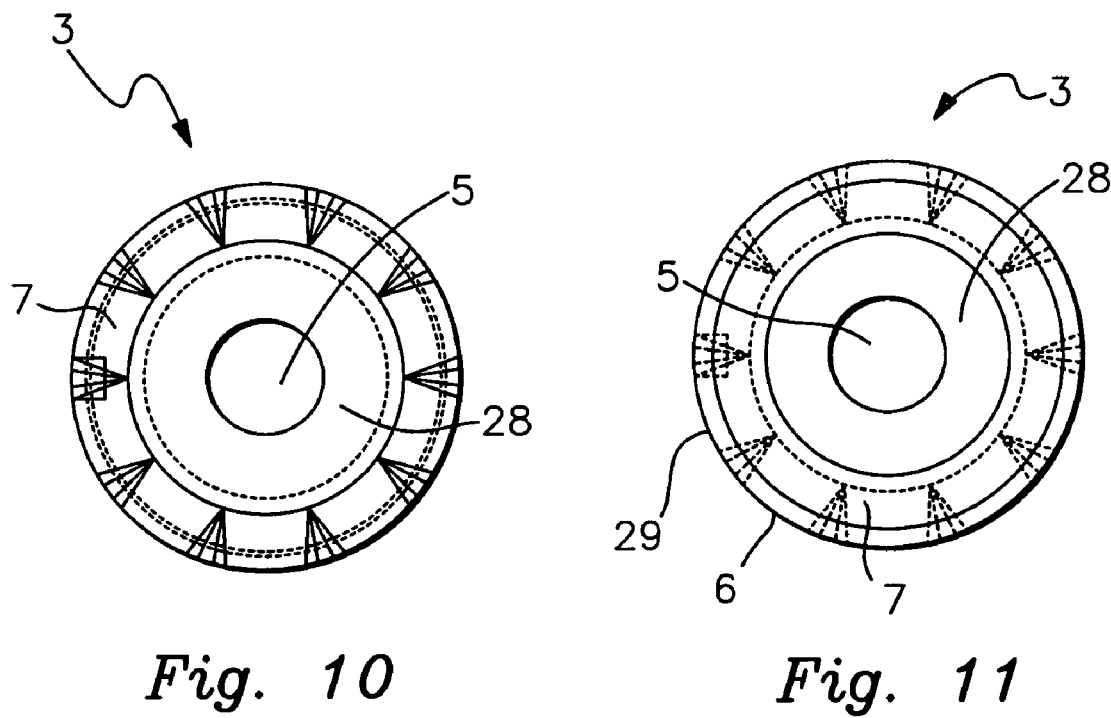
FIG. 10 depicts a top view of end cap 3.
FIG. 11 depicts a bottom view of end cap 3.

FIGS. 9 and 10 show top views of end cap 3 and depict opening 5 formed about the periphery of top wall 28. FIG. 11 shows a bottom view of end cap 3 and depicts the interior side of top wall 28 and opening 5 formed about the periphery of top wall 28. Lug 29 extends from the interior wall of round section 6 and extends inward towards the center of the interior hollow cavity of end cap 3.

FIGS. 13 and 14 show sectional views of adjustable tip 1 as a single assembly with end cap 3 and sleeve 2 combined. Adjustable tip 1 is an assembly wherein end cap 3 is fitted over sleeve 2. Rounded section 12 and tapered section 13 of sleeve 2 are received within the hollow cavity of end cap 3. When fully assembled, distal end 8 of end cap 3 abuts shoulder 16 of sleeve 2 and round section 6 and tapered section 7 of end is cap 3 are substantially parallel with corresponding round section 12 and tapered section 13 of sleeve 2. During assembly, lug 29 slides down tapered section 13 and round section 12 and then snaps into helical groove 17. Once assembled, lug 29 is captured by and difficult to remove from helical groove 17. Accordingly, end cap 3 is captive with sleeve 2. End cap 3 may be rotated up to 180 degrees as lug 29 is guided between the ends of helical groove 17. By twisting end cap 3, lug 29 is guided either upwards or downwards, depending on the directional motion of the twist, and end cap 3 is correspondingly raised or lowered. FIG. 13 depicts end cap 3 maximally extended upwards and away from sleeve 2 as defined by lug 29 positioned at the high end of helical groove 17. FIG. 14 depicts end cap 3 in closest proximity to sleeve 2 as defined by lug 29 positioned at the low end of helical groove 17.

When end cap 3 is raised from sleeve 2, such as is depicted in FIG. 13, a chamber 30 is formed between top wall 28 of end cap 3 and top wall 23 of sleeve 2. Chamber 30 controls the length of needle 27 that will protrude outwards from opening 5. When adjustable tip 1 is used with a lancet device, a patient's skin, such as a finger tip, is positioned adjacent to top wall 28 and exposed over opening 5. The lancet device is then activated and lancet 24 is thrust upward toward opening 5. Shoulder 26 abuts the interior side of top wall 23 and stops further progression of lancet 24. At that moment, needle 27 extends through opening 22 of sleeve 2 and through opening 5 of end cap 3. However, needle 27 will extend fully through opening 22 but not necessarily fully through opening 5. The amount of needle 27 that extends through opening 5 depends upon the position of end cap 3 on sleeve 2. If end cap 3 is in closest proximity to sleeve 2 as depicted in FIG. 14, the maximum amount of needle 27 protrudes from opening 5 and a maximum puncture depth is reached in the patient's skin. When end cap 3 is twisted such that chamber 30 is formed, a limited portion of the outermost tip of needle 27 extends from opening 5 as the remaining section of needle 27 remains in chamber 30. FIG. 13 depicts a maximum extension of end cap 3, thereby maximizing the depth of chamber 30 and reducing the length of needle 27 protruding from opening 5 and consequently minimizing the puncture depth of needle 27 into the patient's skin. The maximum height that end cap 3 may reach is dependent upon the length of helical groove 17. Helical groove 17 can be of any length, including a spiral greater than 360 degrees.

Figure 15:
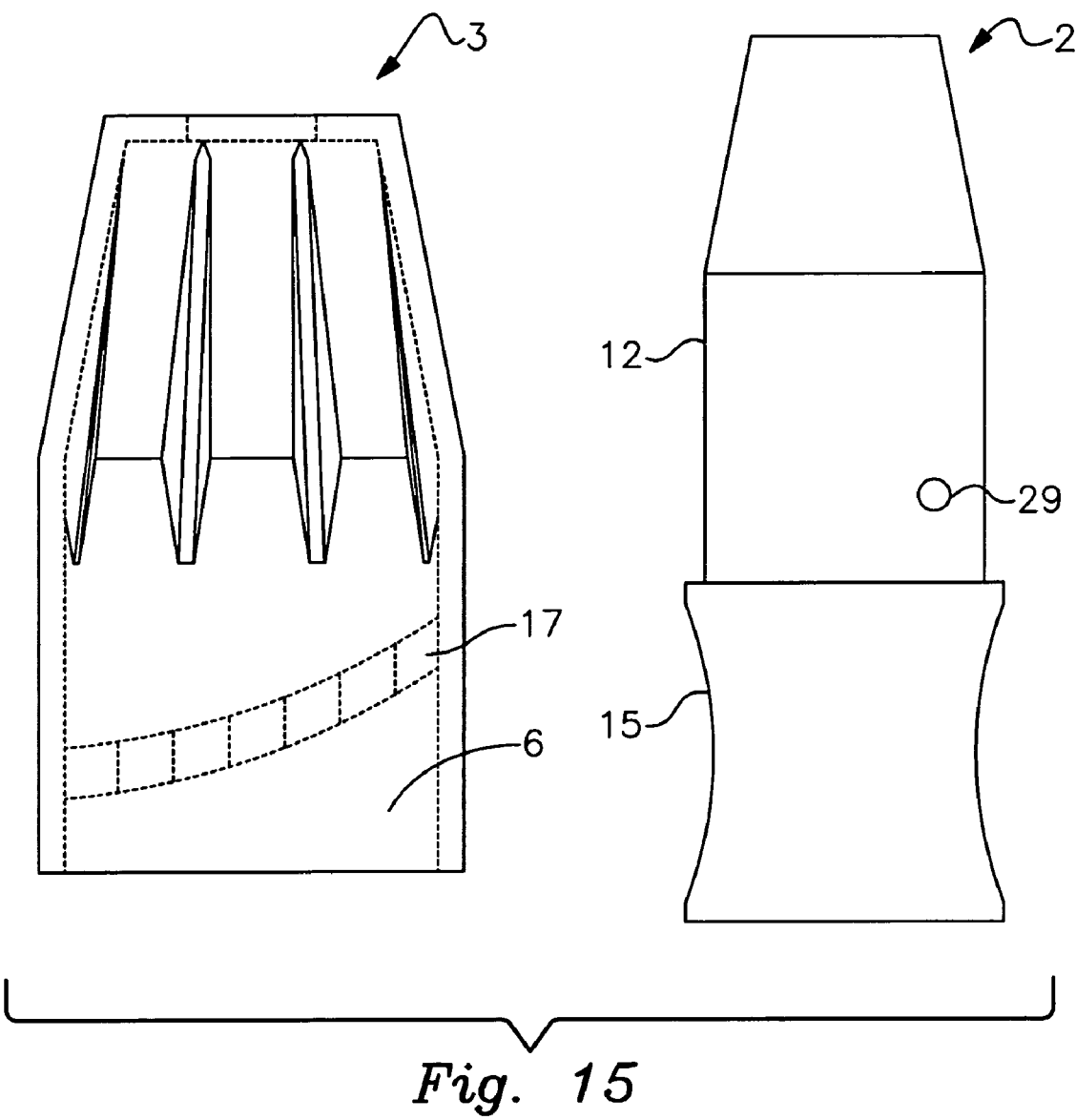
FIG. 15 depicts sleeve 2 having lug 29 and end cap 3 having the helical groove 17.

In an alternative embodiment as illustrated in FIG. 15, the helical groove 17 and the lug 29 are reversed, such that the helical groove 17 is positioned within round section 6 of the end cap 3, and the lug 29 is correspondingly positioned in round section 12 of sleeve 2. Peaks 18 and valleys 19 remain positioned in helical groove 17. In this configuration, adjustable tip 1 operates in the same manner as set forth above and below.

A detent means is used to stabilize a selected penetration depth of needle 27. In the absence of a detent means, the rotation of end cap 3 may unintentionally shift and result in an unintended increase or decrease in puncture depth. According to the preferred embodiment of the present invention, the detent means is comprised of lug 29 and repeating equidistant depressions forming peaks 18 and valleys 19 located on the inside wall of helical groove 17. In the preferred embodiment peaks 18 and valleys 19 are a square shaped repeating pattern. When end cap 3 is twisted, lug 29 moves from one of valleys 19 to the neighboring valley. Peaks 18' are positioned between valleys 19 such that when end cap 3 is twisted, lug 29 travels across one of peaks 18. Each time lug 29 moves across one of peaks 18, lug 29 encounters resistance which is overcome when lug 29 moves into one of valleys 19. Once lug 29 rests in one of valleys 19, the two peaks 18 on each side of lug 29 and between the single valley serve as a detent and prevent unintended movement of lug 29 through helical groove 17 to other positions.

Overcoming the resistance creates an audible click that may be heard and used by the user to verify that the depth setting has been changed by one position. Likewise, the feeling of twisting resistance followed by non-resistance provides a tactile sensation to the user's fingers and another verification that the depth setting has changed by on position. A vibration may be felt in adjustable tip 1 when lug 29 passes over each of peaks 18 which further aids in tactile sensation. The detent means may also include any other structures located within helical groove 17 such as bumps, knobs, fingers, beveling, protrusions, pits, ridges, or any other structures that serve as obstacles to the movement of lug 29. Likewise the detent means may also include such structures located on one or more of the opposing upper and lower walls of helical groove 17. In one such alternative embodiment, the upper and lower walls of helical groove 17 contain alternative ridges, peaks or bumps that resist the movement of lug 29. Lug 29 may move past each such peak by flexing or straining upwards and/or downward. In the alternative embodiment of the present invention where the helical groove is positioned on end cap 3 and lug 29 is positioned on sleeve 2, the detent means is likewise reversed in a similar manner.

In the preferred embodiment, visual indicators 10 are positioned to correspond with the position of lug 29. Particularly, when lug 29 is positioned within one of valleys 19, visual indicators 10 on base 15 and on rounded section 6 are in visual alignment indicating that end cap 3 is stabilized. The preferred embodiment also contains five valleys 19 corresponding to five different depth settings.

While this invention has been described in terms of several embodiments, it is contemplated that alterations, permutations, and equivalents thereof will become apparent to one of ordinary skill in the art upon reading this specification in view of the drawings supplied herewith. It is therefore intended that the invention and any claims related thereto include all such alterations, permutations, and equivalents that are encompassed by the spirit and scope of this invention.

What is claimed is:

1. An adjustable tip for a lancet comprising:
a sleeve having a helical groove;
the helical groove having spaced depressions and opposing side walls;
a one-piece end cap having an interior wall;
the interior wall having a lug;
the end cap positioned over the sleeve such that the lug fits within the helical groove of the sleeve whereby the end cap is secured to the sleeve;
whereby said lug is the only structure securing said end cap to said sleeve, and whereby said lug is sized to fit snuggly within said helical groove such that said helical groove opposing side walls prevent extension or retraction of said end cap relative to said sleeve except when said end cap is rotated relative to said sleeve.

2. The adjustable tip of claim 1, wherein the spaced depressions include peaks and valleys.

3. The adjustable tip of claim 2, wherein the lug resides within one of the valleys.

4. The adjustable tip of claim 1, wherein the helical groove has an inside wall and
opposing side walls, and the spaced depressions are located on the inside wall.

5. The adjustable tip of claim 1, wherein the helical groove has an inside wall and opposing side walls, and the spaced depressions are located on at least one of the opposing side walls.

6. The adjustable tip of claim 1, wherein the helical groove has an inside wall and opposing side walls, and the spaced depressions are located on the inside wall and on at least one of the opposing side walls.

7. The adjustable tip of claim 1, wherein the spaced depressions are substantially evenly spaced to form substantially equidistant and repeating peaks and valleys.

8. The adjustable tip of claim 7, wherein the spaced depressions are substantially square-shaped.

9. The adjustable tip of claim 1, wherein the spaced depressions are comprised of spaced bumps.

10. The adjustable tip of claim 1, wherein the helical groove includes a spiral of at least 180 degrees around a circumference of the sleeve.

11. The adjustable tip of claim 1, wherein the spaced depressions include peaks and valleys and the lug resides within one of the valleys and is movable between valleys whereby a tactile sensory indication is provided when the end cap is rotated about the sleeve and the lug
moves between neighboring valleys.

12. The adjustable tip of claim 1, wherein the spaced depressions include peaks and valleys and the lug resides within one of the valleys and is movable between valleys whereby an audible indication is provided when the end cap is rotated about the sleeve and the lug moves between neighboring valleys.

13. The adjustable tip of claim 1, wherein the end cap twists around and up the sleeve forming a gap between the end cap and the sleeve.

14. The adjustable tip of claim 1, further including visual indicators located on an exterior surface of the end cap and an exterior surface of the sleeve.

15. The adjustable tip of claim 1, wherein the sleeve includes a distal end and a
proximal end, the proximal end having an opening formed in a top wall for receiving a needle.

16. The adjustable tip of claim 15 wherein the end cap includes a distal end and a proximal end, the distal end includes an opening for receiving the sleeve into a hollow cavity formed within the end cap and the proximal end includes an opening for receiving a needle, wherein when the sleeve is received within the end cap the openings in the proximal ends of the sleeve and the end cap are in communicable alignment for receiving a needle through both of the openings.

17. The lancet assembly of claim 15, wherein the end cap includes a distal end and a proximal end, the distal end includes an opening for receiving the sleeve into a hollow cavity formed within the end cap and the proximal end includes an opening formed in a top wall of the end cap and a chamber is formed between the top wall of the end cap and the top wall of the sleeve when the end cap is rotated about the sleeve.

18. The adjustable tip of claim 1, further including a lancing device removably attached to the adjustable tip.

19. The adjustable tip of claim 1, further including a lancing device removably attached to the adjustable tip by an attachment means.

20. An adjustable tip for a lancet comprising:
a sleeve having an exterior sidewall;
a helical groove formed in said exterior sidewall, said helical groove having opposing side walls, an inside wall and spaced depressions;
a one-piece end cap having an interior wall;
a single lug extending from said interior wall of said end cap;
said end cap mounted onto said sleeve such that said lug fits within said helical groove of said sleeve whereby said end cap is secured to said sleeve, whereby upon rotation of said end cap relative to said sleeve said lug moves along said helical groove, thereby extending or retracting said end cap relative to said sleeve, and whereby said spaced depressions retain said lug against accidental movement;
whereby said lug is the only structure securing said end cap to said sleeve, and whereby said lug is sized to fit snuggly within said helical groove such that said helical groove opposing side walls prevent extension or retraction of said end cap relative to said sleeve except when said end cap is rotated relative to said sleeve.

21. The adjustable tip of claim 20, wherein the spaced depressions include peaks and valleys.

22. The adjustable tip of claim 20, wherein said spaced depressions are located on said inside wall of said helical groove.

23. The adjustable tip of claim 20, wherein said spaced depressions are substantially evenly spaced to form substantially equidistant and repeating peaks and valleys.

24. The adjustable tip of claim 23, wherein said spaced depressions are substantially square-shaped.

25. The adjustable tip of claim 23, wherein said spaced depressions are comprised of spaced bumps.

26. The adjustable tip of claim 20, wherein said helical groove
includes a spiral of at least 180 degrees around a circumference of said sleeve.

27. The adjustable tip of claim 20, wherein said spaced depressions include peaks and valleys and said lug resides within one of the valleys and is movable between valleys whereby a tactile sensory indication is provided when said end cap is rotated about said sleeve and said lug moves between neighboring valleys.

28. The adjustable tip of claim 20, wherein said spaced depressions include peaks and valleys and said lug resides within one of the valleys and is movable between valleys whereby an audible indication is provided when said end cap is rotated about said sleeve and said lug moves between neighboring valleys.

29. The adjustable tip of claim 20, wherein said end cap twists around and up said sleeve forming a gap between said end cap and said sleeve.

30. The adjustable tip of claim 20, further having visual indicators located on said end cap and said sleeve.

31. The adjustable tip of claim 20, wherein said sleeve includes a distal end and a proximal end, said proximal end having an opening formed in a top wall for receiving a needle, and further wherein said end cap includes a distal end and a proximal end, said distal end having an opening for receiving the sleeve into a hollow cavity formed within said end cap and said proximal end includes an opening for receiving a needle, wherein when said sleeve is received within said end cap said openings in said proximal ends of said sleeve and said end cap are in communicable alignment for receiving a needle through both of said openings.

32. The adjustable tip of claim 20, further including a lancing device removably attached to said adjustable tip.

* * * * *